US008986975B2

(12) United States Patent
Mester et al.

(10) Patent No.: US 8,986,975 B2
(45) Date of Patent: Mar. 24, 2015

(54) PRODUCTION OF SULFUR-FREE NANOPARTICLES BY YEAST

(75) Inventors: Zoltan Mester, Ottawa (CA); Laurent Ouerdane, Lagor (FR)

(73) Assignee: National Research Council of Canada, Ottawa, ON. (CA)

( * ) Notice: Subject to any disclaimer, the term of this patent is extended or adjusted under 35 U.S.C. 154(b) by 729 days.

(21) Appl. No.: 13/058,655

(22) PCT Filed: Aug. 17, 2009

(86) PCT No.: PCT/CA2009/001155
§ 371 (c)(1),
(2), (4) Date: Feb. 11, 2011

(87) PCT Pub. No.: WO2010/020044
PCT Pub. Date: Feb. 25, 2010

(65) Prior Publication Data
US 2011/0135932 A1 Jun. 9, 2011

Related U.S. Application Data

(60) Provisional application No. 61/136,245, filed on Aug. 21, 2008.

(51) Int. Cl.
| C12P 1/02 | (2006.01) |
| C12P 9/00 | (2006.01) |
| C12P 3/00 | (2006.01) |
| C01B 19/02 | (2006.01) |

(52) U.S. Cl.
CPC . *C12P 3/00* (2013.01); *C01B 19/02* (2013.01); *C01P 2002/85* (2013.01); *C01P 2004/04* (2013.01); *C01P 2004/32* (2013.01); *C01P 2004/61* (2013.01)
USPC .............................. 435/262; 435/41; 435/131

(58) Field of Classification Search
CPC ............... C12P 1/00; C12P 1/02; C12P 3/00; C01B 19/00; C01B 19/02; C01P 2004/00; C01P 2004/60; C01P 2004/61; C01P 2004/62; C01P 2004/64; C01P 2004/32; C01P 2004/45; C02F 2305/00; C02F 2305/08; C02F 1/442
See application file for complete search history.

(56) References Cited

U.S. PATENT DOCUMENTS

2005/0013759 A1* 1/2005 Grow ............................ 423/263

FOREIGN PATENT DOCUMENTS

| EP | 1930063 A1 * | 6/2008 | ............ B01D 47/02 |
| WO | 2006/084276 A2 | 8/2006 | |

OTHER PUBLICATIONS

"Engineer", Datasheet [online]. MedlinePlus, Medical Dictionary-Merriam Webster, Merriam-Webster, Inc., Copyright 2013 [retrieved on Oct. 5, 2013]. Retrieved from the Internet: <URL: http://www.merriam-webster.com/medlineplus/enginneered>.*
"Genetic Engineering", Datasheet [online]. MedlinePlus, Medical Dictionary-Merriam Webster, Merriam-Webster, Inc., Copyright 2013 [retrieved on Oct. 5, 2013]. Retrieved from the Internet: <URL: http://www.merriam-webster.com/medlineplus/genetic%20engineering>.*
"Oxidation State", Datasheet [online]. Univ. of Waterloo, Canada. Chem Dept. [retrieved on Oct. 5, 2013]. Retrieved from the Internet: <URL: http://www.science.uwaterloo.ca/~cchieh/cact/c123/oxidstat.html>.*
Shen, Z. et al. 2011. Improved drug targeting of cancer cells by utilizing actively targetable folic acid-conjugated albumin nanospheres. Pharmacological Research 63:51-58. specif. pp. 51, 52.*
American Heritage Stedman's Medical Dictionary (Wild type. Datasheet [online]. Copyright 2002, 2001, 1995. Houghton Mifflin Company [retrieved on Mar. 11, 2014]. Retrieved from the Internet: <URL: http://dictionary.reference.com/browse/wild+type>. p. 2.*
Soccol, C.R. et al. Flavor Compounds Produced by Fungi, Yeasts, and Bacteria. In: Handbook of Food Products Manufacturing. Y.H. Hui, ed. Copyright 2007. John Wiley & Sons, Inc. Hoboken, New Jersey. pp. 179-192. specif. p. 199.*
BD Biosciences (Sabouraud Liquid Broth. Datasheet [online]. Page last revised May 1, 2006. Copyright 2013. Becton Dickinson and Company [retrieved on Oct. 3, 2013]. Retrieved from the Internet: <URL: http://www.bd.com/ds/productCenter/221014.asp> pp. 1-2.*
BD Bionutrients Technical Manual. Bacto Tryptone and Peptone. In chapters: "Meat Peptones" and "Casein and Whey Peptones". 3rd ed. revised. Oct. 2006. Becton Dickinson and Company.p. 36 and 48.*
Wikipedia (*Schizosaccharomyces pombe*. Datasheet [online]. Page last modified on Mar. 16, 2014. Wikimedia Foundation, Inc. [retrieved on Mar. 29, 2014]. Retrieved from the Internet: <URL: http://en.wikipedia.org/wiki/Schizosaccharomyces_pombe> p. 1.*
European Extended Search Report dated Jun. 5, 2012 on European application 09807787.8.
International Search Report and Written Opinion on International Application PCT/CA2009/001155 mailed Nov. 24, 2009.
Abelovska L, Bujdos M, Kubova J, Petrerselyova S, Nosek J, Tomaska L. (2007) Comparison of element levels in minimal and complex yeast media. Can. J. Microbiol. 53, 533-535.
Agnihorti M, et al. (2009) Biosynthesis of gold nanoparticles by the tropical marine yeast *Yarrowia lipolytica* NCIM 3589. Materials Letters. 63, 1231-1234.
Dameron CT, Reese RN, Mehra RK, Kortan AR, Carroll PJ, Steigerwald ML, Brus LE, Einge DR. (1989) Biosynthesis of cadmium sulphide quantum semiconductor crystallites. Nature. 338, 596-597.
Gericke M, Pinches A. (2006) Biological synthesis of metal nanoparticles. Hydrometallurgy 83, 132-140.
He W, et al. (2009) Biominerlization of Iron Phosphate Nanoparticles in Yeast Cells. Materials Science and Engineering C. 29, 1348-1350.

(Continued)

*Primary Examiner* — John S Brusca
*Assistant Examiner* — Sharon M Papciak
(74) *Attorney, Agent, or Firm* — Jason E. J. Davis

(57) ABSTRACT

A method of producing sulfur-free nanoparticles involves growing yeast in a growth medium containing a source of an element in a bio-reducible oxidation state (e.g. Se(VI), and, precipitating nanoparticles containing the element in a lower oxidation state (e.g. Se(O)) than the oxidation state of the element in the source. The method advantageously can provide substantially spherical nanoparticles at high production efficiencies.

20 Claims, 2 Drawing Sheets

(56) References Cited

OTHER PUBLICATIONS

Kowshik M, et al. (2003) Extracellular Synthesis of Silver Nanoparticles by a Silver-tolerant Yeast Strain MKY3. Nanotechnology. 14, 95-100.

Krumov N, Oder S, Perner-Nochta I, Angelov A, Posten C. (2007) Accumulation of CdS nanoparticles by yeasts in a fed-batch bioprocess. Biotechnol. 132(4), 481-486.

Krumov N, et al. (2009) Production of Inorganic Nanoparticles by Microorganisms. Chem. Eng. Technol. 32(7), 1026-1035.

Ma LQ, et al. (2001) A fern that hyperaccumulates arsenic. Nature. 409, 579.

Mandal D, Bolander ME, Mukhopadhyay D, Sarkar G. Mukherjee P. (2006) The use of microorganisms for the formation of metal nanoparticles and their application. Applied Microbiology and Biotechnology 69, 485-492.

Sherman F. (2002) Getting started with yeast. Methods Enzymol. 350, 3-41.

* cited by examiner

PRODUCTION OF SULFUR-FREE NANOPARTICLES BY YEAST

CROSS-REFERENCE TO RELATED APPLICATIONS

This application is a national stage entry of International Patent Application PCT/CA2009/001155 filed Aug. 17, 2009 and claims the benefit of U.S. Provisional Patent Application Ser. No. 61/136,245 filed Aug. 21, 2008, the entire contents of both of which are herein incorporated by reference.

FIELD OF THE INVENTION

The present invention relates to methods of producing sulfur-free nanoparticles and to sulfur-free nanoparticles so produced.

BACKGROUND OF THE INVENTION

Yeast is one of the most commonly used biological systems for trace element enrichment for human nutrition and animal feed. Selenium enriched yeast along with synthetic selenomethionine and inorganic selenium salts are used for Se supplementation. The majority of selenium in selenium enriched yeast is selenomethionine a non-canonical amino acid, analog of methionine. However the chemical form of the remaining 30% of the Se in these yeast formulations are largely unknown. There are many reports in the peer reviewed literature describing other sulfur analogs of selenium in yeast however only one single paper claims that these "other Se species" (manly thiol analogs: selenols) are actually representing the "missing" 30% of selenium.

There is an ever growing interest in the synthesis of nanomaterials due to their physical, chemical and photoelectrochemical properties (Gericke, 2006). The synthesis of nanomaterials over a range of chemical composition and high monodispersity is still challenging in material science. Many of the technologies available for the production of nanomaterials are chemically and often energetically intensive. Biological production of these nanomaterials could represent a green alternative to the synthetic protocols used nowadays. It has been known for decades that many biological systems from plants to uni-cellular organism can accumulate large quantities of metallic elements (Gericke, 2006). The entire field of bioremediation is based on this notion. Plants such as those from genus *Salicornia* can collect Se from marshlands and volatilize it. Other plants, such as *Pteris vittata* (Ma, 2001), accumulate enormous quantities of arsenic, uranium, etc. forming insoluble inorganic deposits in the extracellular space effectively detoxifying them.

The use of microorganism for the intra or extracellular production of nanomaterials has been recently reviewed by Mandal et al. (Mandal, 2006). Bacteria has been reported to produce gold, silver, cadmium sulfide, magnetite nanoparticles, and, certain yeast species have been reported to produce cadmium and lead sulfide nanoparticles (Dameron, 1989; Krumov, 2007), where Cd starts and ends in the +2 oxidation state.

Inductively couple plasma mass spectrometry is the analytical tool of choice in trace and ultra trace metal analysis. However, like most mass spectrometry based wet chemical analytical strategies, ICP MS is usually used for bulk analysis. Typical sample sizes are in the milligram to gram range. When spatial resolution requires smaller sample sizes the analytical sampling and sample introduction typically moves away from wet chemistry and employs for example lasers for sampling and sample introduction. Laser ablation (LA) ICP MS is able to provide spatial resolution in the 5-10 micron range enabling applications such as tissue imaging in the biological realm. Recent developments in near field laser ablation could result in even sub-optical resolutions. However in order to study subcellular distribution of trace elements and potentially nanoparticles, submicron spatial resolution is necessary.

There remains a need in the art for a simple, environmentally friendly method of producing bulk quantities of nanoparticles, especially selenium nanoparticles.

SUMMARY OF THE INVENTION

It has now been surprisingly found that yeast may be used to produce sulfur-free nanoparticles.

Thus, there is provided a method of producing sulfur-free nanoparticles comprising: growing yeast in a growth medium containing a source of an element in a bio-reducible oxidation state; and, precipitating nanoparticles containing the element in a lower oxidation state than the oxidation state of the element in the source.

Yeasts are eukaryotic microorganisms classified in the kingdom Fungi, with about 1,500 species currently described. Yeasts are classified in phylum Ascomycota. Preferred yeasts are classified in subphylum Saccharomycotina. More preferred yeasts are from the class Saccharomycetes, particularly from the order Saccharomycetales, the budding yeasts. Particularly preferred are yeasts from family Saccharomycetaceae, in particular from genus *Saccharomyces*, for example, *Saccharomyces bayanus*, *Saccharomyces boulardii*, *Saccharomyces bulden*, *Saccharomyces cariocanus*, *Saccharomyces cariocus*, *Saccharomyces cerevisiae*, *Saccharomyces chevalieri*, *Saccharomyces dairenensis*, *Saccharomyces ellipsoideus*, *Saccharomyces martiniae*, *Saccharomyces monacensis*, *Saccharomyces norbensis*, *Saccharomyces paradoxus*, *Saccharomyces pastorianus*, *Saccharomyces spencerorum*, *Saccharomyces turicensis*, *Saccharomyces unisporus*, *Saccharomyces uvarum*, *Saccharomyces zonatus*. A very particularly preferred species is *Saccharomyces cerevisiae*. *Saccharomyces cerevisiae* (baker's yeast) is common, inexpensive, easy to grow and provides surprisingly excellent nanoparticle production efficiencies.

In the source, the element exists in an oxidation state that is reducible to a lower oxidation state by action of the yeast. Without being held to any particular mode of action, it is thought that yeast bio-reduces the element from a higher oxidation state to a lower oxidation state, thereby precipitating the element as nanoparticles. The precipitated nanoparticles may contain the element in elemental form having a 0 oxidation state or may contain compounds of the element in a lower but positive oxidation state. Nanoparticles containing the element in the 0 oxidation state are particularly observed. The nanoparticles may be produced intracellularly or extracellulary, intracellular production is particularly observed.

The element may be, for example, a metal, a non-metal, a semi-metal or a mixture thereof. Metals include main group metals, transition metals, lanthanide series metals and actinide series metals. Main group metals include, for example, Group IIIA metals (e.g. gallium, indium, tantalum), Group IVA metals (e.g. tin, lead and Group VA metals (e.g. bismuth). Transition metals include, for example, Group VIII metals (e.g. iron, rhodium, nickel, palladium, platinum) and Group IB metals (e.g. copper, silver, gold). Lanthanide series metals include, for example, lanthanum, cerium, neodymium and ytterbium. Actinide series metals include, for example, thorium and uranium. Non-metals include main groups elements, for example, Group VIA elements like selenium but not sulfur. Semi-metals (metalloids) include main group elements, for example, Group IVA elements (e.g. silicon and germanium), Group VA elements (e.g. arsenic and antimony) and Group VIA elements (e.g. tellurium).

Preferred sources of the element comprise Group VIII elements, Group IB elements, Group VIA elements or mixtures thereof, especially selenium, tellurium, arsenic, gallium, germanium, antimony, gold, silver, palladium, platinum or mixtures thereof. Selenium, gold, silver, platinum, palladium or mixtures thereof are particularly preferred. Preferably, the source is an inorganic source, for example, oxygen, nitrogen and/or phosphorus compounds, especially oxygen compounds. Particularly preferred sources include selenates, tellurates, gallates, germinates, antimonates, aurates, argentates, palladinates, platinates or mixtures thereof.

The source of the element is preferably present in the medium in an amount of about 1 ppm to about 1000 ppm, more preferably about 5-500 ppm, for example about 10-100 ppm. Generally, the source of the element should not be present in an amount that is too toxic for the yeast. For example, a convenient upper limit on the amount of the source of the element is the LD50 of the element.

The growth medium comprises various compounds necessary for the successful growth of the yeast. Such media are generally well known in the art (Sherman, 2002; Abelovska, 2007). Yeast are generally grown in the laboratory on solid growth media or liquid broths. Broths are preferred. Common, commercially available media used for the cultivation of yeasts include, for example, Sabouraud medium, potato dextrose (PD), Wallerstien Laboratories Nutrient (WLN), Yeast Extract Peptone Dextrose (YEPD), Yeast Mould (YM) and molasses. Many of the commercially available media are based on fungus peptone or yeast extracts, and contain sources of sulfur and possibly selenium. Therefore, fully defined synthetic media, preferably optimized for the yeast in use, may be preferred to control sulfur during yeast growth. Such media include many of the nutrients and other compounds present in typical media, but without sulfur or selenium sources or with only controlled amounts of sulfur sources. Nutrients and other compounds present in synthetic media include, for example, salts (e.g. $H_2 KPO_4$, $MgCl_2$, NaCl, $CaCl_2$), nitrogen sources (e.g. $NH_4Cl$, amino acids and nitrogen bases), carbohydrate sources (e.g. sugars, for example, dextrose or unsulfured molasses), vitamins (e.g. vitamin B's such as biotin) and trace elements (e.g. boron, zinc, iron). Because some sulfur may be needed for proper growth of the yeast, controlled amounts of a sulfur source (e.g. cysteine) may be added to the otherwise sulfur-free medium in amounts that do not interfere with nanoparticle formation.

Yeast may be grown under aerobic or anaerobic conditions. Aerobic conditions are preferred with oxygen preferably maintained in a range of about 8-15 ppm. Temperature is generally maintained in a range of about 10° C. to about 37° C., preferably about 25° C. to about 37° C., for example about 28° C. to about 30° C. The pH is generally slightly acidic, preferably in a range of about 4-6, more preferably in the range of about 4.5-5.5.

Growth of the yeast may be conducted under batch or continuous conditions, preferably batch conditions, for a sufficient length of time to produce nanoparticles. The time may be, for example, on the order of hours to months. Several days is a generally suitable length of time. The nanoparticles may then be collected by any suitable method, for example, by destruction of the yeast cell membranes followed by one or more of filtration, centrifugation, magnetic separation or other separation technique.

Advantageously, production efficiency of nanoparticles is very high permitting relatively easy scale-up of the process. Production efficiencies of at least 100 µg nanoparticles per gram of yeast, even production efficiencies of at least 250 µg/g, are attainable. Production efficiencies of up to 500 µg/g have been measured.

Nanoparticles of the present invention may comprise a single element or a mixture of elements (e.g. binary or ternary nanoparticles). While nanoparticles that are formed may be of any shape (e.g. spheres, rods), it is a surprising advantage of the present invention that the nanoparticles that are formed can be substantially spherical. Previously in the art, it has been difficult to produce spherical nanoparticles. Average particle diameters in a range of about 1-500 nm, more particularly in a range of about 10-100 nm or about 25-75 nm are achievable in the present invention. Size distribution on the order of about ±30 nm are typical for bulk samples.

Sulfur-free nanoparticles advantageously contain less than 0.1 wt % sulfur, for example less than 0.05 wt % sulfur.

Nanoparticles produced by the method of the present invention may find uses in a variety of applications requiring nanomaterials, for example, in quantum dots or other electronic devices.

Further features of the invention will be described or will become apparent in the course of the following detailed description.

BRIEF DESCRIPTION OF THE DRAWINGS

In order that the invention may be more clearly understood, embodiments thereof will now be described in detail by way of example, with reference to the accompanying drawings, in which.

DESCRIPTION OF PREFERRED EMBODIMENTS

Figure 1A:
FIG. 1A depicts a transmission electron microscopy (TEM) image of selenium nanoparticles produced in accordance with the present invention (scale in bottom left corner is 1 µm)

Materials and Methods:
Yeast
A wild-type strain of baker's yeast, *Saccharomyces cerevisiae*, was isolated (selected after being grown in a Petri dish) and used in all experiments. All chemicals were of analytical grade and compatible with cell cultures.
Mass Spectrometry
An ELAN™ DRC II ICPMS (PE-Sciex, Thornhill, ON, Canada) equipped with a Ryton™ spray chamber and cross-flow nebulizer was used for the detection of selenium and sulfur. Hydrogen was used as a collision gas and ICPMS parameters, nebulizer gas flow, rf power, lens voltages, and hydrogen gas flow, were optimized daily to get the best S/N ratio for S and Se. A Hewlett-Packard HP 6890 GC (Agilent Technologies Canada Inc., Mississauga, ON, Canada) fitted with a DB-5MS column (Iso-Mass Scientific Inc., Calgary AB, Canada) was used for the separation of methionine (Met) and selenomethionine (SeMet) in the derivatized yeast extracts. Detection was achieved with an HP model 5973 mass-selective detector (MS). A CEM (Matthews, N.C.) MDS-2100 microwave digester equipped with Teflon™ vessels was used for closed vessel high pressure decomposition of yeast for total Se and S determination.

Example 1

Production of Se Nanoparticles in Synthetically Defined Growth Medium 1

As commercially prepared yeast growth media, such as YEPD, are usually based on fungus peptone or yeast extracts, they contain many sources of sulfur and possibly selenium. Therefore, a synthetically defined medium optimized for *S. cerevisiae* was prepared to control sulfur during yeast growth. All prepared media had the same chemical constituents except that sources of sulfur and selenium were varied.

Salts ($MgCl_2$, NaCl, $CaCl_2$), nitrogen source ($NH_4Cl$), phosphorus source ($KH_2PO_4$) and carbohydrate source (dextrose) were mixed together in an appropriate volume of water to obtain the final concentrations shown in Table 1. This solution was then autoclaved at 121° C. for 35 min and stored aseptically. After the mixture cooled, previously prepared vitamins, trace elements and amino acid solutions were added with syringes through 0.2 µm sterile filters to reach the final concentrations detailed in Table 1. The latter were added to the medium through syringes and filters after the media was autoclaved to prevent their denaturation. Supplementary additions of selenium compounds to the medium for nanoparticle formation were also made through syringes and 0.2 µm sterile filters. All manipulations of glassware containing growth media and/or yeast were performed inside a laminar flow hood and the manipulating tools were sterilized with a flame or in the autoclave.

TABLE 1

Composition of Defined Growth Medium 1

| | Chemicals | Concentration (mg/L) |
|---|---|---|
| Carbohydrate/Sugar | Dextrose | 20,000 |
| Nitrogen | $NH_4Cl$ | 5000 |
| Salts | $MgCl_2$ | 500 |
| | NaCl | 100 |
| | $CaCl_2$ | 100 |
| Phosphorus | $KH_2PO_4$ | 1000 |
| Sulfur | L-Cysteine | 10 |
| Amino acids | Adenine | 10 |
| | L-Arginine, HCl | 50 |
| | L-Aspartic acid | 80 |
| | L-Histidine | 20 |
| | L-Isoleucine | 50 |
| | L-Leucine | 100 |
| | L-Lysine, HCl | 50 |
| | L-Phenylalanine | 50 |
| | L-Threonine | 100 |
| | L-Tryptophan | 50 |
| | L-Tyrosine | 50 |
| | Uracil | 20 |
| | L-Valine | 140 |
| Vitamins mix | Biotin | 0.002 |
| | Pantothenate, Ca | 0.4 |
| | Folic acid | 0.002 |
| | Inositol | 2 |
| | Nicotinic acid (niacin) | 0.4 |
| | PABA | 0.2 |
| | Pyridoxine, HCl | 0.4 |

TABLE 1-continued

Composition of Defined Growth Medium 1

| | Chemicals | Concentration (mg/L) |
|---|---|---|
| | Riboflavin | 0.2 |
| | Thiamine, HCl | 0.4 |
| Trace elements mix | $H_3BO_3$ | 0.5 |
| | $CuCl_2$ | 0.04 |
| | $FeCl_3$ | 0.2 |
| | $MnCl_2$ | 0.4 |
| | $Na_2MoO_4$ | 0.2 |
| | $ZnCl_2$ | 0.4 |
| | $Na_2EDTA$ | 15 |
| | KI | 0.1 |

Yeast cells were stabilized using glutaraldehyde buffer (0.1M phosphate buffer at pH 6.7 containing 4% glutaraldehyde) for chemical fixation. After incubation (5 min) and centrifugation (1500 g, 4 min), the supernatant is discarded and the cells are re-suspended in 1 mL of glutaraldehyde buffer diluted twice. The cells are incubated overnight at 4° C. After centrifugation, the supernatant is replaced by 1.5 ml of deionised water, incubated in water (10 min) and centrifuged. This re-suspension/centrifugation is repeated 3 times. Finally, the cells are re-suspended in 1 mL of deionised water.

Yeast was grown in batch conditions (an Erlenmeyer flask) in a fully defined synthetic growth medium comprising the medium described above including 0.08 mM cysteine and 0.4 mM sodium selenate or SeMet. The growth medium was free of sulfur sources except for the cysteine. The temperature was held at 28° C. and the flask shaken at 150 rpm for up to five days.

Under these conditions the yeast metabolized inorganic selenium (sodium selenate in which Se is in the +6 oxidation state) forming selenomethionine (a non-canonical amino acid) which is incorporated into the yeast proteome in the place of methionine. Under these growth conditions, total Se concentration in the yeast was 2.4 mg/g (as dry weight). About 65-70% of the total Se was in the form of selenomethionine, as determined using electrospray and inductively coupled plasma mass spectrometry, replacing about one out of four methionines. However, using electrospray and inductively coupled plasma mass spectrometry the remaining 30% of Se could not be accounted for.

With yeast grown on SeMet-containing media full replacement of Met with SeMet was observed and virtually 100% of the total Se in these samples was in the form of SeMet.

Figure 1B:
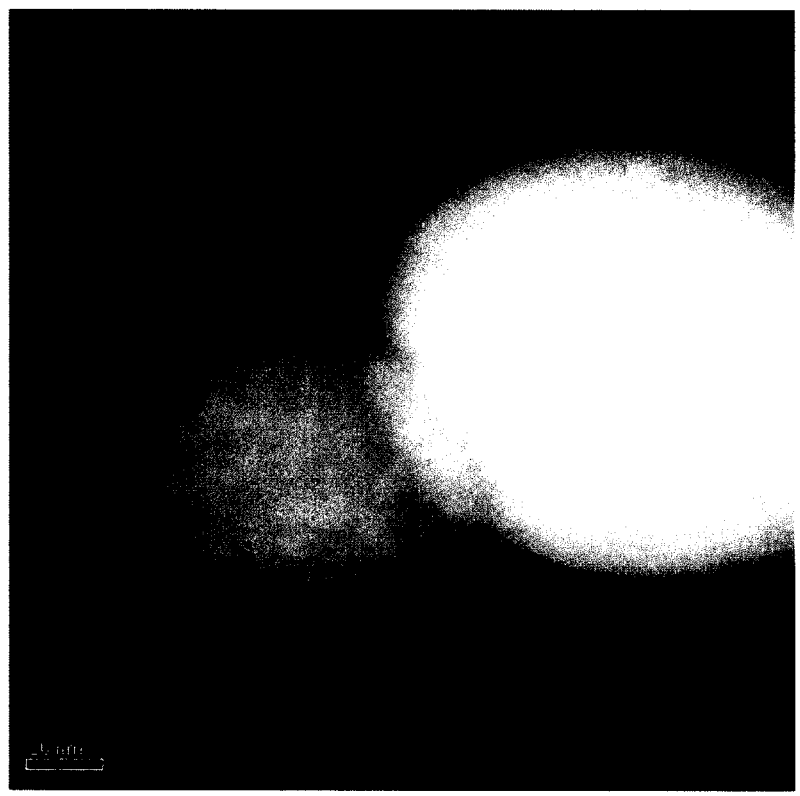
FIG. 1B depicts a transmission electron microscopy (TEM) image of selenium nanoparticles produced in accordance with the present invention (scale in bottom left corner is 20 nm); and, FIG. 2 depicts an energy-dispersive X-ray spectrum (EDS) of thin sections of yeast grown in sulfur-free sodium selenate-containing media.
Figure 2:
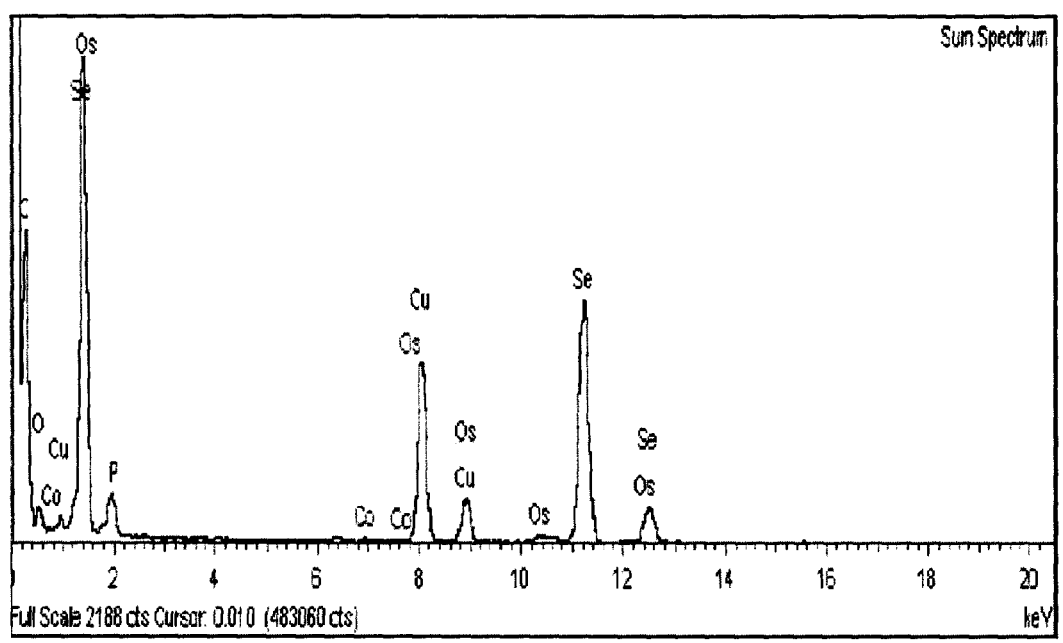

Transmission electron microscopy (TEM) studies of microtomed thin sections of yeast grown in sulfur-free sodium selenate-containing media indicated the presence of electron dense spots in the cells, indicating the presence of nanoparticles. Energy-dispersive X-ray spectrometry (EDS) analysis was used to determine elemental composition of these deposits. EDS analysis revealed that the composition of these nanoparticles is elemental Se, i.e. Se in the 0 oxidation state. The nanoparticles are spherical having an average size in the 50 nm range. Transmission electron microscopy (TEM) images depicted in FIG. 1A (scale at bottom left corner is 1 µm) and FIG. 1B (scale at bottom left corner is 20 nm) show the Se nanoparticles identified in the cells at various magnification. The presence of fringes indicated that the selenium particles may be composed of nanocrystals. However the chemically and mechanically intensive sample preparation required for TEM could raise questions about contamination or potentially the formation of such deposits during the chemical treatment or sectioning process. Additionally, the EDS analysis of the cells allowed only detection of highly concentrated Se spots, i.e. Se nanoparticles (FIG. 2).

In contrast the TEM analysis of yeast grown on SeMet showed no nanoparticle formation. This is expected because in these samples all the selenium is in the form of SeMet and SeMet is replacing Met in the yeast proteome. Interestingly the only location in the cell where any Se could be detected with EDS is the nuclear membrane.

Example 2

Production of Nanoparticles in Synthetically Defined Growth Medium 2

A second synthetically defined growth medium optimized for *S. cerevisiae* was prepared to control sulfur during yeast growth. All prepared media had the same chemical constituents except that sources of metal for nanoparticle production were varied.

Salts ($MgCl_2$, NaCl, $CaCl_2$), nitrogen source ($NH_4Cl$), phosphorus source ($KH_2PO_4$) and carbohydrate source (dextrose) were mixed together in 850 ml of water to obtain the final concentrations shown in Table 2. This solution was then autoclaved at 121° C. for 45 min and stored aseptically. After the mixture cooled, previously prepared vitamins, trace elements and amino acid solutions were added with syringes through 0.2 μm sterile filters to reach the final concentrations detailed in Table 2. The latter were added to the medium through syringes and filters after the medium was autoclaved to prevent their denaturation. Supplementary additions of metal compounds to the medium for nanoparticle formation were also made through syringes and 0.2 μm sterile filters. All manipulations of glassware containing growth media and/or yeast were performed inside a laminar flow hood and the manipulating tools were sterilized with a flame or in the autoclave.

TABLE 2

Composition of Defined Growth Medium 2

| | Chemicals | Concentration (mg/L) |
|---|---|---|
| Carbohydrate/Sugar | Dextrose | 4000 |
| Nitrogen | $NH_4Cl$ | 5000 |
| Salts | $MgCl_2$ | 500 |
| | NaCl | 100 |
| | $CaCl_2$ | 100 |
| Phosphorus | $KH_2PO_4$ | 1000 |
| Sulfur | L-Cysteine | 10 |
| Amino acids | Adenine | 10 |
| | L-Arginine, HCl | 50 |
| | L-Aspartic acid | 80 |
| | L-Histidine | 20 |
| | L-Isoleucine | 50 |
| | L-Leucine | 100 |
| | L-Lysine, HCl | 50 |
| | L-Phenylalanine | 50 |
| | L-Threonine | 100 |
| | L-Tryptophan | 50 |
| | L-Tyrosine | 50 |
| | Uracil | 20 |
| | L-Valine | 140 |
| Vitamins mix | Biotin | 0.002 |
| | Pantothenate, Ca | 0.4 |
| | Folic acid | 0.002 |
| | Inositol | 2 |
| | Nicotinic acid (niacin) | 0.4 |
| | PABA | 0.2 |
| | Pyridoxine, HCl | 0.4 |
| | Riboflavin | 0.2 |
| | Thiamine, HCl | 0.4 |
| Trace elements mix | $H_3BO_3$ | 0.5 |
| | $CuCl_2$ | 0.04 |
| | $FeCl_3$ | 0.2 |

TABLE 2-continued

Composition of Defined Growth Medium 2

| Chemicals | Concentration (mg/L) |
|---|---|
| $MnCl_2$ | 0.4 |
| $Na_2MoO_4$ | 0.2 |
| $ZnCl_2$ | 0.4 |
| $Na_2EDTA$ | 15 |
| KI | 0.1 |

Yeast cells were stabilized using glutaraldehyde buffer for chemical fixation. 50 mL of the medium containing the growing yeast is collected and centrifuged (3000×g) for 3 min. The supernatant is discarded, the cells resuspended in the same volume of doubly distilled water (DDW) and centrifuged again (3000×g) for 3 min. This resuspension/centrifugation in DDW is repeated 3 times. It is then resuspended in 10 mL DDW. A volume of 100 μL of the sample is mixed with 900 μL of a 0.1 M phosphate buffer pH 6.7 containing 4% glutaraldehyde and allowed to incubate for 5 minutes. Then, it is centrifuged at 2000×g for 4 min, the supernatant discarded and the cells resuspended in 1 mL of a 0.05 M phosphate buffer (pH 6.7) containing 2% glutaraldehyde. The sample is incubated overnight at 4° C., then centrifuged (3000×g) for 4 min. The supernatant is discarded, the cells resuspended with 1.5 ml of DDW, incubated in water for 10 min and centrifuged again (3000×g) for 4 min. This resuspension/centrifugation in DDW is repeated 3 times, and the cells resuspended in 1 mL DDW.

Trial 1: Yeast was grown on 50 ml of defined medium 2 for 26 hours at 150 rpm at a temperature of 28° C. or 25° C. Various metal compounds were then added with syringes through a 0.2 μm sterile filter to different batches of the medium to achieve final concentrations as follows: Ag (I) 10 ppm; Au(III) 10 ppm; Pt(II) 10 ppm; Te(VI) 4 ppm; Se(IV) 4 ppm. After about 60 hours of yeast growth, formation of nanoparticles was confirmed for Ag by visual inspection of a color change in the growth medium. No color changes in the growth media for Au, Pt, Te and Se were observed, probably due to the low concentrations of metals used, but nanoparticle formation was confirmed through microscopic observations.

Trial 2: Yeast was grown on defined medium 2 for 10 hours at 150 rpm at a temperature of 28° C. or 25° C. Various metal compounds were then added to different 50 ml batches of the medium to achieve final concentrations as follows: Ag (I) 10 ppm; Au(III) 10 ppm; Pt(II) 10 ppm; Pd(II) 10 ppm; Se(IV) 5 ppm. The pH of the metal solutions was adjusted to 4 with $NH_4OH$, except for Au which was adjusted to 2-3. After about 60 hours of yeast growth, no color changes in the growth media were observed, again probably due to the low concentrations of metals used, but nanoparticle formation was confirmed through microscopic observations.

Example 3

Production of Nanoparticles in Sabouraud Dextrose Broth

Sabouraud dextrose broth is a commercially available growth medium for yeast which comprises 20.00 g/L dextrose and 10.0 g/L of a mixture of peptic of animal tissue and pancreatic digest of casein (1:1). The final broth is prepared by suspending 30 grams of the medium in one liter of distilled water and mixing well until a uniform suspension is obtained. The mixture is heated with frequent agitation, boiled for one minute, distributed and sterilized at 118-121° C. for 15-45 minutes. The final pH is 5.6±0.2 at 25° C.

Yeast cells were stabilized using glutaraldehyde buffer for chemical fixation. 50 mL of the medium containing the growing yeast is collected and centrifuged (3000×g) for 3 min. The supernatant is discarded, the cells resuspended in the same volume of doubly distilled water (DDW) and centrifuged again (3000×g) for 3 min. This resuspension/centrifugation in DDW is repeated 3 times. It is then resuspended in 10 mL DDW. A volume of 100 µL of the sample is mixed with 900 µL of a 0.1 M phosphate buffer pH 6.7 containing 4% glutaraldehyde and allowed to incubate for 5 minutes. Then, it is centrifuged at 2000×g for 4 min, the supernatant discarded and the cells resuspended in 1 mL of a 0.05 M phosphate buffer (pH 6.7) containing 2% glutaraldehyde. The sample is incubated overnight at 4° C., then centrifuged (3000×g) for 4 min. The supernatant is discarded, the cells resuspended with 1.5 ml of DDW, incubated in water for 10 min and centrifuged again (3000×g) for 4 min. This resuspension/centrifugation in DDW is repeated 3 times, and the cells resuspended in 1 mL DDW.

Trial 1: Yeast was grown in Sabouraud dextrose broth for 26 hours at 150 rpm at a temperature of 28° C. or 25° C. Various metal compounds were then added with syringes through a 0.2 µm sterile filter to different 100 ml batches of the medium to achieve final concentrations as follows: Ag (I) 40 ppm; Au(III) 20 ppm; Pt(II) 40 ppm; Te(VI) 20 ppm; Se(IV) 20 ppm. After about 60 hours of yeast growth, formation of nanoparticles was confirmed for all of the metals by visual inspection of a color change in the growth medium and through microscopic observations.

Trial 2: Yeast was grown in Sabouraud dextrose broth for 10 hours (for Pd, Ag, Au, Pt, U, Se) or for 24.5 hours (for Cd, Zn, Pb) at 150 rpm at a temperature of 28° C. or 25° C. Various metal compounds were then added to different 100 ml batches of the medium to achieve final concentrations as follows: Pd(II) 50 ppm; Ag (I) 50 ppm; Au(III) 50 ppm; Pt(II) 50 ppm; U(VI) 50 ppm; Se(IV) 20 ppm; Cd(II) 50 ppm; Zn(II) 50 ppm; Pb(IV) 50 ppm. The pH of the metal solutions was adjusted to 4 with $NH_4OH$, except for Au which was adjusted to 2-3. After about 60 hours of yeast growth, formation of nanoparticles was confirmed for Ag and Au by visual inspection of a color change in the growth medium. No color changes in the growth media for other metals were observed, but nanoparticle formation was confirmed through microscopic observations.

Trial 3: Two replicates of 0.1 ml of yeast and two replicates of 0.2 ml of yeast were added to four bottles of Sabouraud broth. After growing at 25° C. (150 rpm) for 16.5 h, Se (IV) was added to the yeast samples (with syringes through 0.2 µm sterile filter) to reach final concentrations of 20, 50, 150 ppm, respectively. 52.5 h after addition of Se (IV), samples were collected and freezing dried. Visual inspection of color change in the medium demonstrated that greater quantities of nanoparticles were formed at the higher concentrations compared to the lower concentrations.

References: The contents of the entirety of each of which are incorporated by this reference.

Abelovska L, Bujdos M, Kubova J, Petrerselyova S, Nosek J, Tomaska L. (2007) Comparison of element levels in minimal and complex yeast media. *Can. J. Microbiol.* 53, 533-535.

Dameron C T, Reese R N, Mehra R K, Kortan A R, Carroll P J, Steigerwald M L, Brus L E, Einge D R. (1989) Biosynthesis of cadmium sulphide quantum semiconductor crystallites. *Nature.* 338, 596-597.

Gericke M, Pinches A. (2006) Biological synthesis of metal nanoparticles. *Hydrometallurgy* 83, 132-140.

Grow A E. (Jan. 20, 2005) Practical Method for Preparing Inorganic Nanophase Materials. United States Patent Publication 2005-013759.

Krumov N, Oder S, Perner-Nochta I, Angelov A, Posten C. (2007) Accumulation of CdS nanoparticles by yeasts in a fed-batch bioprocess. *Biotechnol.* 132(4), 481-486.

Ma L Q, et al. (2001) A fern that hyperaccumulates arsenic. *Nature* 409, 579.

Mandal D, Bolander M E, Mukhopadhyay D, Sarkar G. Mukherjee P. (2006) The use of microorganisms for the formation of metal nanoparticles and their application. *Applied Microbiology and Biotechnology* 69, 485-492.

Sherman F. (2002) Getting started with yeast. *Methods Enzymol.* 350, 3-41.

Other advantages that are inherent to the structure are obvious to one skilled in the art. The embodiments are described herein illustratively and are not meant to limit the scope of the invention as claimed. Variations of the foregoing embodiments will be evident to a person of ordinary skill and are intended by the inventor to be encompassed by the following claims.

The invention claimed is:

1. A method of producing sulfur-free nanoparticles comprising: growing a wild-type yeast strain from genus *Saccharomyces* in a growth medium containing a source of an element in a bio-reducible oxidation state; and, precipitating nanoparticles containing the element from the source in a lower oxidation state than the oxidation state of the element in the source, where the element is a metal, a semi-metal, or selenium.

2. The method according to claim 1, wherein the source comprises an inorganic source.

3. The method according to claim 2, wherein the element is selenium, gold, silver, platinum, palladium or a mixture thereof.

4. The method according to claim 2, wherein the element is selenium.

5. The method according to claim 1, wherein the source of the element comprises selenate, aurate, argentate, platinate, palladate or a mixture thereof.

6. The method according to claim 1, wherein the source of the element comprises selenate.

7. The method according to claim 1, wherein the lower oxidation state is 0 oxidation state.

8. The method according to claim 1, wherein the yeast strain comprises *Saccharomyces cerevisiae*.

9. The method according to claim 1, wherein the growth medium is a fully defined synthetic growth medium.

10. The method according to claim 1, wherein the growth medium is sulfur-free except for addition of a controlled amount of a sulfur source.

11. The method according to claim 1, wherein the growth medium comprises Sabouraud medium, potato dextrose, Wallerstien Laboratories Nutrient, Yeast Extract Peptone Dextrose, Yeast Mould or molasses.

12. The method according to claim 1, wherein the growth medium comprises Sabouraud medium.

13. The method according to claim 1, wherein the nanoparticles are produced intracellularly.

14. The method according to claim 1 conducted in a batch reactor.

15. A method of producing sulfur-free nanoparticles comprising: growing a wild-type yeast strain in a growth medium containing a source of an element in a bio-reducible oxidation state; and, precipitating nanoparticles containing the element from the source in a lower oxidation state than the oxidation state of the element in the source, where the element is a metal, a semi-metal, or selenium, and the nanoparticles are produced in an amount of at least 100 µg nanoparticles per gram of yeast.

16. The method according to claim 1, wherein the nanoparticles are produced in an amount of 100-500 µg nanoparticles per gram of yeast.

17. A method of producing sulfur-free nanoparticles comprising:

growing a wild-type yeast strain in a growth medium containing a source of an element in a bio-reducible oxidation state; and, precipitating nanoparticles containing the element from the source in a lower oxidation state than the oxidation state of the element in the source, where the element is a metal, a semi-metal, or selenium, and the source of the element comprises selenate platinate, palladate or a mixture thereof.

18. The method of claim 15 wherein:
the source comprises an inorganic source;
the source of the element comprises selenate, aurate, argentate, platinate, palladate or a mixture thereof;
the source of the element comprises selenate;
the element is selenium, gold, silver, platinum, palladium or a mixture thereof;
wherein the element is selenium;
the lower oxidation state is 0 oxidation state;
the yeast strain comprises a species from phylum Ascomycota;
the yeast strain comprises a species from a genus *Saccharomyces;*
the yeast strain comprises *Saccharomyces cerevisiae;*
the growth medium is a fully defined synthetic growth medium;
the growth medium is sulfur-free except for addition of a controlled amount of a sulfur source;
the growth medium comprises Sabouraud medium, potato dextrose, Wallerstien Laboratories Nutrient, Yeast Extract Peptone Dextrose, Yeast Mould or molasses;
the growth medium comprises Sabouraud medium;
the nanoparticles are produced intracellularly; or the method is conducted in a batch reactor.

19. The method of claim 17 wherein:
the element is selenium, gold, silver, platinum, palladium or a mixture thereof;
the element is selenium;
the lower oxidation state is 0 oxidation state;
the yeast strain comprises a species from phylum Ascomycota;
the yeast strain comprises a species from a genus *Saccharomyces;*
the yeast strain comprises *Saccharomyces cerevisiae;*
the growth medium is a fully defined synthetic growth medium;
the growth medium is sulfur-free except for addition of a controlled amount of a sulfur source;
the growth medium comprises Sabouraud medium, potato dextrose, Wallerstien Laboratories Nutrient, Yeast Extract Peptone Dextrose, Yeast Mould or molasses;
the growth medium comprises Sabouraud medium;
the nanoparticles are produced intracellularly;
the method is conducted in a batch reactor;
the nanoparticles are produced in an amount of at least 100 µg nanoparticles per gram of yeast; or the nanoparticles are produced in an amount of 100-500 µg nanoparticles per gram of yeast.

20. The method of claim 15, wherein the element is selenium, gold, silver, platinum, palladium or a mixture thereof.

* * * * *